United States Patent [19]
Rastegar et al.

[11] Patent Number: 5,882,299
[45] Date of Patent: Mar. 16, 1999

[54] DEVICE AND PROCEDURE FOR MINIMALLY INVASIVE CORONARY ANASTOMOSIS

[75] Inventors: Hassan Rastegar; Dermot Halpin, both of Boston, Mass.; Peter Rosendahl; Steven LeVahn, both of St. Paul, Minn.

[73] Assignee: Minnesota Scientific, Inc., Minneapolis, Minn.

[21] Appl. No.: 792,253

[22] Filed: Jan. 31, 1997

[51] Int. Cl.[6] .................................................. A61B 17/00
[52] U.S. Cl. ........................................... 600/232; 128/898
[58] Field of Search .................................. 600/201, 227, 600/228, 229, 231, 232, 235; 128/898

[56] References Cited

U.S. PATENT DOCUMENTS

| | | |
|---|---|---|
| Re. 34,150 | 12/1992 | Santilli et al. . |
| 2,642,862 | 6/1953 | Jackson ................................... 600/232 |
| 2,670,732 | 3/1954 | Nelson . |
| 3,710,783 | 1/1973 | Jascalevich . |
| 4,616,635 | 10/1986 | Caspar et al. . |
| 4,813,401 | 3/1989 | Grieshaber . |
| 4,829,985 | 5/1989 | Couetil . |
| 4,852,552 | 8/1989 | Chaux . |
| 4,865,019 | 9/1989 | Phillips ................................... 600/232 |
| 4,946,463 | 8/1990 | Wright ..................................... 600/158 |
| 4,989,587 | 2/1991 | Farley . |
| 5,025,779 | 6/1991 | Bugge . |
| 5,363,841 | 11/1994 | Coker . |
| 5,452,733 | 9/1995 | Sterman et al. . |
| 5,503,617 | 4/1996 | Jako ......................................... 600/201 |
| 5,571,215 | 11/1996 | Sterman et al. ........................... 623/66 |
| 5,651,378 | 7/1997 | Matheny et al. ......................... 128/898 |
| 5,676,636 | 10/1997 | Chin ................................... 600/235 X |

FOREIGN PATENT DOCUMENTS 1456108   2/1989   U.S.S.R. ................................ 600/232

OTHER PUBLICATIONS

*The Journal of Thoracic and Cardiovascular Surgery*, vol. 111, No. 3, Mar. 1996, pp. 566–573.

*Primary Examiner*—Jeffrey A. Smith
*Attorney, Agent, or Firm*—Kinney & Lange, P.A.

[57] ABSTRACT

A minimally invasive coronary anastomosis procedure includes providing an incision in an intercostal space between two ribs of a patient, the incision providing access to a selected anastomosis site on a blocked coronary artery. A spreader device is inserted between the two ribs, the spreader device spreading the two ribs apart to sufficiently widen the incision for the procedure to be performed through the incision. An internal mammary artery is dissected from the thoracic wall, and the heart is pharmaceutically treated to substantially reduce its heartbeat. The blocked coronary artery is clamped at two spaced-apart positions at the selected anastomosis site. The blocked coronary artery is incised, and the dissected internal mammary artery is sutured to the incision at the anastomosis site.

11 Claims, 3 Drawing Sheets

DEVICE AND PROCEDURE FOR MINIMALLY INVASIVE CORONARY ANASTOMOSIS

BACKGROUND OF THE INVENTION

The present invention relates to coronary anastomosis procedures, and in particular, it relates to minimally invasive coronary anastomosis procedures.

Coronary arterial diseases remain one of the leading causes of mortality. The disease may be manifested by insufficient blood flow resulting in angina, myocardial infarction and death.

A number of approaches have been developed and used for treating coronary arterial diseases. Pharmaceuticals and lifestyle changes are used in less severe cases to lessen the progression of the disease. Coronary blockage in more severe cases is often treated endovascularly using techniques such as balloon angioplasty, atheroectomy, laser ablation, stents and hot tip probes.

In cases where the above-mentioned treatments have failed or will not likely result in reducing or eliminating the blockage, often times a coronary artery bypass graft procedure is performed using the traditional open surgical techniques. Typically, using such a technique, the patient's sternum is opened and the chest is spread apart to provide the surgeon access to the heart. A source of arterial blood is then connected to the coronary artery distal to the occlusion. Typically the heart is stopped using potassium cardioplegia and perfusion to the vital organs is supported by cardiopulmonary bypass. The source of arterial blood is often the left or right internal mammary artery (IMA).

This traditional approach is effective in relieving angina and restoring blood flow to the heart, however cardiopulmonary bypass being non-pulsatile in nature has been associated with neurophysiological disorders, stroke, renal failure, and liver disfunction. Patients typically spend two to three months recuperating before returning to work. Often times the patient cannot even drive for four to six weeks after such surgery since their chests have been severely opened.

One of the problems in performing coronary surgery is providing the surgeon sufficient access to the surgical area. Human anatomy provides the coronary area protection through the sternum, the rib cage and the costal cartilages. However, the same protective structure provides a barrier and a problem for the surgeon in performing coronary surgery. In the past, surgeons have simply cut through the sternum or the rib cage to provide access into the thoracic cavity. Sawing or cutting such structure has obvious traumatic effects on the patient.

Less traumatic procedures have been developed recently. For example, the Sterman et al. U.S. Pat. No. 5,452,733 describes a thoracoscopic coronary artery bypass procedure. This procedure uses several trocar sheaths such as used in conventional laporascopic procedures to provide access into the patient's chest and to provide access for a viewing scope. However, the bypass procedure is utilizing cardioplegia to arrest the heart and cardiopulmonary bypass to perfuse the vital organs prior to connecting the arterial graft to the coronary artery.

Similarly, the Sterman et al. U.S. Pat. No. 5,571,215 describes a method and devices for performing less-invasive arterial surgical procedures. A scope is positioned through a percutaneous intercostal penetration in the patient's chest to provide a view within the patient's chest. Through another percutaneous penetration in an intercostal space in the patient's chest, a tool is inserted to perform the surgical procedure. Again, prior to the percutaneous penetrations, the patient's heart is arrested and placed on cardiopulmonary bypass.

A number of devices have been developed for retracting bones and tissue in cardiovascular surgery. Such devices are described in the Santilli et al. Re. No. 34,150, Couetil U.S. Pat. No. 4,809,985, Chaux U.S. Pat. No. 4,852,552, Farley U.S. Pat. No. 4,989,587 and Bugge U.S. Pat. No. 5,025,779. Other devices similar in construction but useful for different surgical procedures are also disclosed in the Coker U.S. Pat. No. 5,363,841, Grieshaber U.S. Pat. No. 4,813,401, the Casper et al. U.S. Pat. No. 4,616,635, the Jascalvich U.S. Pat. No. 3,701,783 and the Nelson U.S. Pat. No. 2,670,732.

Another minimally invasive coronary bypass procedure is described in an article in the Minneapolis Star and Tribune dated Sep. 19, 1995 which describes a procedure titled "*Trap Door Procedure*" for performing a bypass operation in which the heart is not placed under cardiopulmonary bypass. The entry into the chest cavity is a three-inch-long opening in the lower breast bone. The heartbeat is reduced to 35 beats per minute through the use of pharmaceuticals. The IMA is clamped and is dissected for use as the bypass to restore blood flow to the heart. The blocked coronary artery is clamped and a slit is made into the artery distal to the occlusion. The IMA is sutured to the blocked coronary artery over the slice. Eight sutures are made between heartbeats and left loose until all sutures are in place. The sutures are then pulled tight and tied to close the two arteries together. Although this minimally invasive procedure results in less trauma and a reduced hospital stay along with reduced costs then previous prior art procedures, it is still somewhat traumatic since the incision is made through the breast bone.

SUMMARY OF THE INVENTION

The present inventions including a minimally invasive coronary anastomosis procedure includes providing an incision in an intercostal space between two ribs of a patient, the incision providing access to a selected anastomosis site on a blocked coronary artery. A spreader device is inserted between the two ribs, the spreader device spreading the two ribs apart to sufficiently widen the incision for the procedure to be performed through the incision. The internal mammary artery is dissected from the thoracic wall, and the heart is pharmaceutically treated to substantially reduce its heartbeat. The blocked coronary artery is clamped at two spaced-apart positions at the selected anastomosis site. The blocked coronary artery is incised, and the dissected internal mammary artery is sutured to the incision at the anastomosis site.

DETAILED DESCRIPTION OF THE PREFERRED EMBODIMENTS

The present invention includes a minimally invasive coronary bypass procedure in which a minimum amount of trauma is placed on the patient. The method relies on the direct visualization of the internal mammary artery (IMA) and is performed on the beating heart of the patient without the aid of cardiopulmonary bypass.

Figure 1:
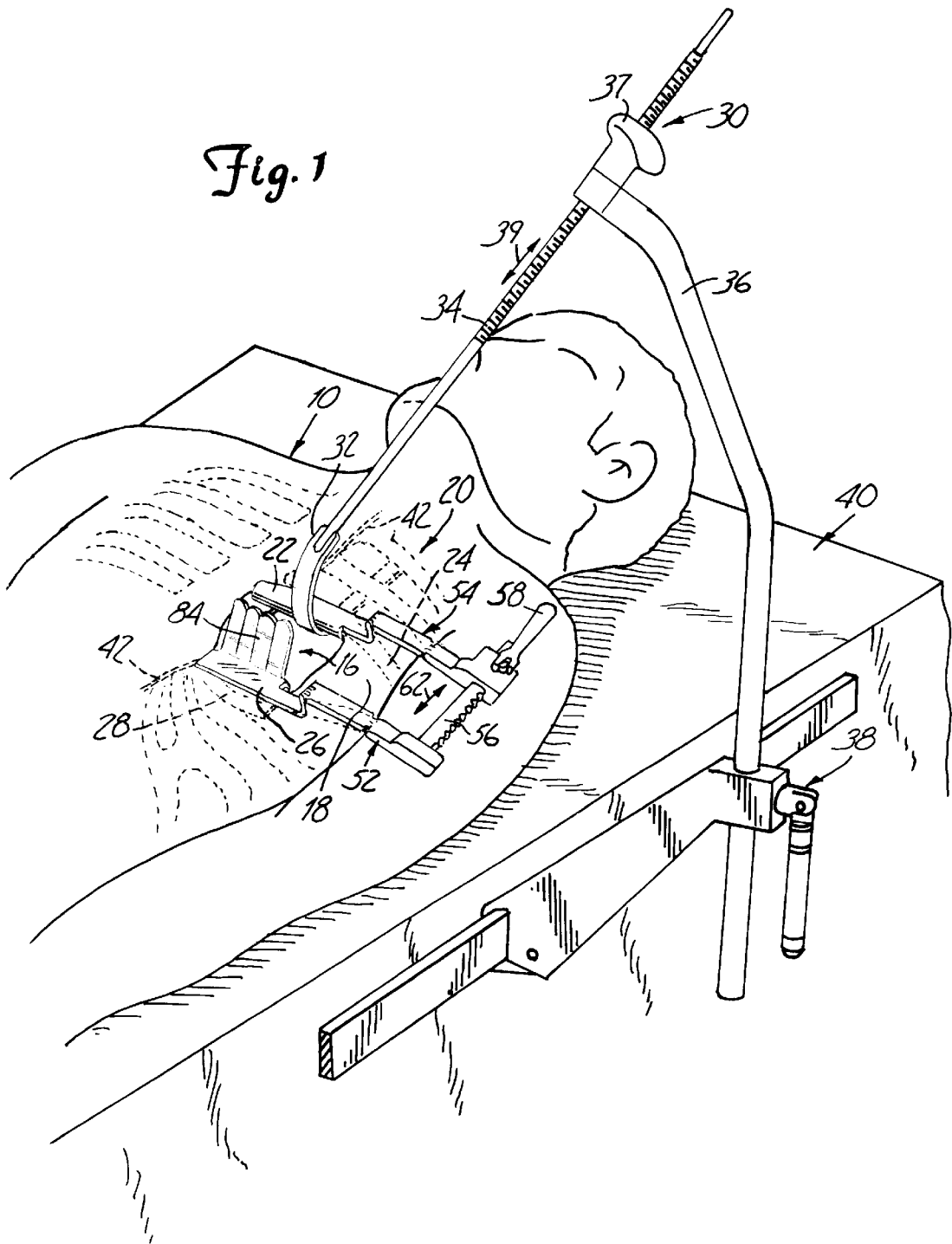
FIG. 1 is a perspective view illustrating the present invention in use.

As illustrated in FIG. 1, the procedure includes placing a patient 10 in a supine position. A 7 cm transverse incision 16 is made in the fourth intercostal space 18. A rib spreader device 20 of the present invention having an upper retractor blade 22 for engaging a third rib 24 and a lower retractor blade 26 for engaging a fourth rib 28 is positioned within the incision. The device 20 is then operated to spread the incision open by engaging the third and the fourth ribs.

Figure 2:
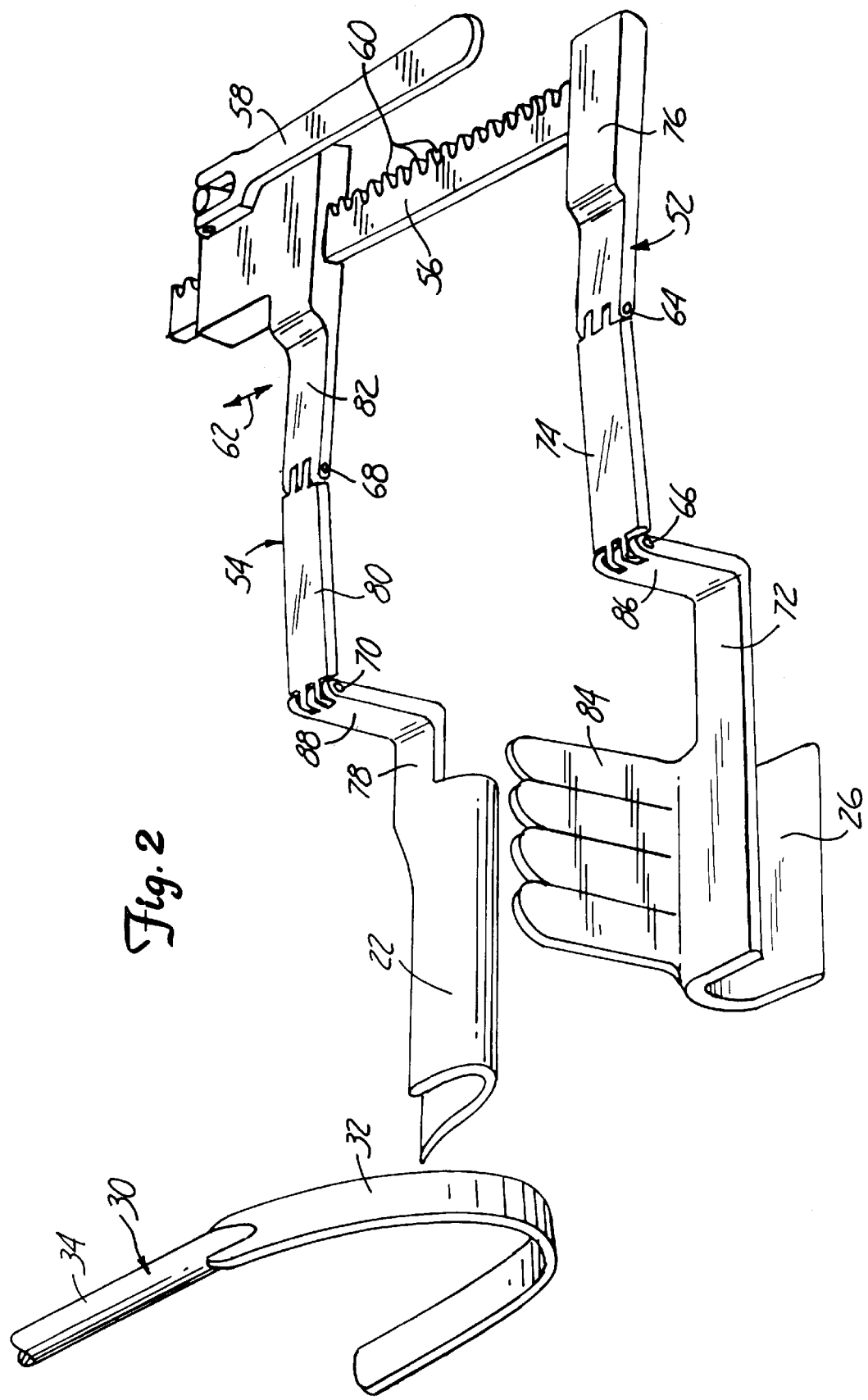
FIG. 2 is a perspective view of a surgical retractor device of the present invention.

The device 20 as best illustrated in FIG. 2, includes a lower arm 52 that includes the lower retractor blade 26 and an upper arm 54 that includes the upper retractor blade 22. The lower arm 52 is connected to a rack bar 56 that is disposed within the arm 54. A pinion member (not shown) which is drivably operable by handle 58 engages teeth 60 of the rack bar 56 thereby moving the arm 54 in a direction indicated by arrows 62. This movement spreads the ribs apart and opens the incision 16 as discussed above.

Each arm 52 and 54 includes hinge sections 64, 66 and hinge sections 68, 70, respectively. The hinge sections divide each respective arm into three pivotable members. For example, lower arm 52 includes a lower arm blade member 72, a lower arm mid-member 74 and a lower arm rack bar engaging member 76. Similarly, the upper arm 54 includes an upper arm blade member 78, and upper arm mid-member 80 and an upper arm rack bar engaging member 82. The lower arm blade member 72 further includes a plurality of generally upright extending fingers 84 and a proximally disposed generally upright extending section 86. Similarly, the upper arm blade member 78 also includes a proximally disposed generally upwardly extending section 88.

The hinged feature of the device 20 permits the device through the hinge sections to accommodate those patients having thicker than normal chest tissue layers. The device 20 has the capability of engaging the ribs through use of the blades 26 and 22 and while being disposed in a comfortable and convenient manner on top of the patient, away from the incision due to the hinged sections 64, 66, 68 and 70 as illustrated in FIG. 1.

The purpose of the fingers 84 are to retain fatty tissue layers away from the incision. Although the device illustrated in the drawings only includes finger sections on the blade 26, it is within the scope of the present invention to include such finger layers both on the lower blade member 72 and on the upper blade member 78.

Once the incision is spread apart using the device 20, a retractor lifter 30 is positioned to engage the upper retractor blade 22 of the device 20. The retractor lifter 30 includes a blade member 32, a threaded shank section 34 and a table post section 36. A handle 37 is rotatably mounted to the post section 36 and includes internally disposed threads that engage the threaded shank section 34. By turning handle 37, the lifter device moves in the general direction of arrows 39.

The table post section 36 is secured to the operating table 40 by a clamping mechanism 38. The retractor lifter through the blade 32 lifts the upper rib cage of the patient 10. The lifting of the rib cage exposes IMA 42 such that the IMA is directly visible to the surgeon. The IMA is exposed from the fourth intercostal space up to its origin at the subclavian artery. The entire IMA is separated from the thoracic wall from the fourth intercostal space up to the subclavian artery. All branches of the IMA are ligated and divided.

Once the IMA is harvested, the retractor lifter 30 is operated to lower the device 20 and is disengaged from the upper retractor blade 22. The upper rib cage then comes to rest at its normal level.

Figure 3:
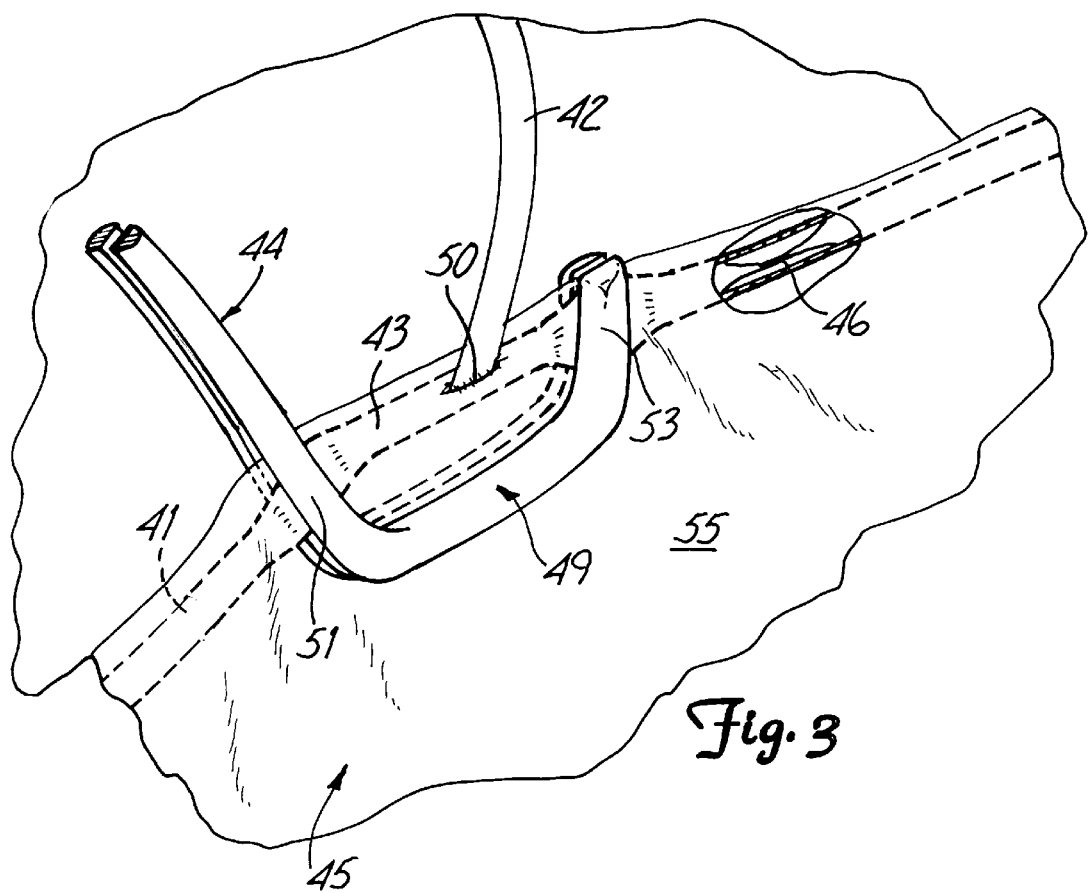
FIG. 3 is a perspective view illustrating a blocked artery being clamped for suturing using clamping forceps of the present invention.

The heartbeat of the patient is pharmaceutically reduced to about 35 beats per minute. The blocked artery 41 with blockage 46 and the anastomosis site 43 are identified. The anastomosis site 43 which is disposed downstream from the blockage 46 is doubly clamped using forceps 44, as illustrated in FIG. 3. The forceps includes a clamping section 49 that is U-shaped which clamps the site 43 in two spaced-apart positions 51 and 53. The blocked artery, for example the left anterior descending artery, is typically contained within tissue membrane 55 along the surface of the heart 45. Even though the beating of the heart has been minimized, since the blocked artery 41 is contained within the outer membrane surface of the heart, the movement of the heart along with the position of the artery presents a difficult suturing condition.

Doubly clamping the anastomosis site 43 of the artery 41 results in more favorable suturing conditions. Doubly clamping the anastomosis site aids in immobilizing the anastomosis site from the remainder of the beating heart. Clamping the anastomosis site and in effect pinching also brings the anastomosis site nearer to the surface of the heart membrane tissue. Clamping also minimizes the amount of blood that is still flowing through the blockage 46. After clamping, a slit 50 is made into the anastomosis site 43 of the artery 41. The IMA 42 is then sutured to the blocked artery 41 at the site 43. The sutures are secured and the clamping forceps 44 are removed.

Although the present invention has been described with reference to preferred embodiments, workers skilled in the art will recognize that changes may be made in form and detail without departing from the spirit and scope of the invention.

What is claimed is:

1. A minimally invasive coronary anastomosis procedure for a blocked coronary artery of a heart, the procedure comprising:

providing an incision in an intercostal space between two ribs of a patient, the incision providing access to a selected anastomosis site;

inserting a spreader device between the two ribs, the spreader device having a first end for engaging the first rib and a second end for engaging the second rib;

lifting the spreader device such that the second and juxtaposed ribs are elevated with respect to the first rib thereby exposing an internal mammary artery sufficiently for direct visualization;

dissecting the internal mammary artery; and performing the anastomosis through the incision using the internal mammary artery.

2. The procedure of claim 1 wherein the patient is positioned on a surgical table, and wherein the spreader device is lifted using a lifting mechanism that is mounted to the surgical table and extends upwardly to a position above the patient.

3. The procedure of claim 1 and further including:

treating the heart pharmaceutically to substantially reduce heartbeat;

clamping the blocked coronary artery at the selected anastomosis site at two spaced-apart positions; and suturing the internal mammary artery to an incision made in the blocked artery while the heart is beating at a reduced rate.

4. A minimally invasive coronary anastomosis procedure for a blocked coronary artery of a heart, the procedure comprising:

providing an incision in an intercostal space between two juxtaposed ribs of a patient, the incision providing access to a selected anastomosis site on the blocked coronary artery;

inserting a spreader device between the two juxtaposed ribs such that when the spreader device is operated, the ribs are spread apart widening the incision;

dissecting an internal mammary artery;

treating the heart pharmaceutically to substantially reduce the heartbeat;

clamping the blocked coronary artery at two spaced-apart positions at the selected anastomosis site;

incising the blocked coronary artery downstream from the blockage; and suturing the dissected internal mammary artery to the incision on the blocked coronary artery at the selected anastomosis site.

5. The procedure of claim 4 wherein the patient is positioned on a surgical table, and wherein the spreader device is lifted using a lifting mechanism that is mounted to the surgical table and extends upwardly to a position above the patient.

6. The procedure of claim 4 wherein the dissected internal mammary artery is sutured between the two spaced-apart clamped positions on the occluded coronary artery.

7. A device for use in a surgical procedure in which an incision is made between two juxtaposed ribs of a patient, the device comprising:

a first arm member having a proximal end portion and a distal end portion, the distal end portion having a rib engaging blade, and the distal and proximal end portions being hingedly attached to each other;

a second arm member having a proximal end portion and a distal end portion, the distal end portion having a rib engaging blade and the distal and proximal end portions being hingedly attached to each other;

a mechanism that operably connects the first and the second arm members at the proximal end such that the arm members are movable toward and away from each other; and a retractor lifting device, the device comprising a blade portion for engaging the blade of the second arm member, and a post member secured to an operating table on which the patient lies, and a handle section to which the blade section is movably attached, and a mechanism for moving the blade portion in an upward direction thereby lifting the blade of the second arm member which results in lifting a section of the patient's ribs.

8. The device of claim 7 wherein the mechanism includes a rack bar fixedly attached to the first arm member at one end and at another end movably engages the proximal end portion of the second arm member such that the second arm member moves away and toward the first arm member along the rack bar.

9. The device of claim 7 wherein the first arm member further includes two hinge sections and a mid-section that is hingedly attached to the proximal end portion at one end and to the distal end portion at another end.

10. The device of claim 7 wherein the second arm member further includes two hinge sections and a mid-section that is hingedly attached to the proximal end portion at one end and to the distal end portion at another end.

11. The device of claim 7 wherein the distal end portion of the first arm member further includes a plurality of fingers extending away from the blade for retaining fatty tissue away from the incision.

* * * * *

UNITED STATES PATENT AND TRADEMARK OFFICE
CERTIFICATE OF CORRECTION

PATENT NO. : 5,882,299
DATED : MARCH 16, 1999
INVENTOR(S) : HASSAN RASTEGAR ET AL.

It is certified that error appears in the above-identified patent and that said Letters Patent is hereby corrected as shown below:

Col. 1, line 12, delete "infarction" and insert --infraction--

Col. 1, line 19, delete "atheroectomy" and insert --atherectomy--

Col. 1, line 60, delete "perfuse" and insert --profuse--

Signed and Sealed this

Nineteenth Day of October, 1999

Attest:

Q. TODD DICKINSON

*Attesting Officer*     *Acting Commissioner of Patents and Trademarks*